United States Patent [19]

Richardson et al.

[11] Patent Number: 4,584,307
[45] Date of Patent: Apr. 22, 1986

[54] ANTIFUNGAL 2-ARYL-2-HYDROXY PERFLUORO-1-(1H-1,2,4-TRIAZOL-1-YL) ALKANONES AND ALKANOLS

[75] Inventors: Kenneth Richardson; Peter J. Whittle, both of Canterbury, Great Britain

[73] Assignee: Pfizer Inc., New York, N.Y.

[21] Appl. No.: 631,120

[22] Filed: Jul. 16, 1984

[30] Foreign Application Priority Data

Aug. 10, 1983 [GB] United Kingdom ............... 8321527
Feb. 8, 1984 [GB] United Kingdom ............... 8403279

[51] Int. Cl.$^4$ ............... A01N 43/653; C07D 249/08; C07D 401/06
[52] U.S. Cl. ............... 514/383; 260/665 G; 546/276; 548/262; 514/340; 560/60
[58] Field of Search ............... 514/340, 383; 546/276; 548/262

[56] References Cited

U.S. PATENT DOCUMENTS 3,974,174  8/1976  Buchel et al. ............... 548/262
3,983,240  9/1976  Buchel et al. ............... 514/383
3,993,765  11/1976 Buchel et al. ............... 514/383

FOREIGN PATENT DOCUMENTS 0114487  8/1984  European Pat. Off. ............ 548/262
0114567  8/1984  European Pat. Off. ............ 548/262
0117578  9/1984  European Pat. Off. ............ 548/262
2242454  3/1974  Fed. Rep. of Germany ...... 548/341
2130584  6/1984  United Kingdom ............... 548/262

Primary Examiner—Alton D. Rollins
Attorney, Agent, or Firm—Charles J. Knuth; Albert E. Frost; Peter C. Richardson

[57] ABSTRACT

A fungicidal agent of the formula:

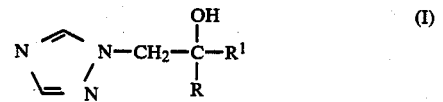

(I)

or a pharmaceutically or agriculturally acceptable salt thereof, wherein R is 5-chloropyrid-2-yl or a phenyl group optionally substituted by 1 to 3 substituents each independently selected from F, Cl, Br, I, $CF_3$, $C_1$-$C_4$ alkyl and $C_1$-$C_4$ alkoxy;

and

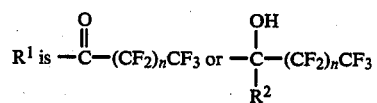

where n is 0, 1, 2 or 3 and $R^2$ is H or $C_1$-$C_4$ alkyl.

13 Claims, No Drawings

ANTIFUNGAL 2-ARYL-2-HYDROXY PERFLUORO-1-(1H-1,2,4-TRIAZOL-1-YL) ALKANONES AND ALKANOLS

BACKGROUND OF THE INVENTION

1. Field of the Invention

This invention relates to novel triazole derivatives which have antifungal activity and are useful in the treatment of fungal infections in animals, including humans, and as agricultural fungicides.

2. Description of the Prior Art

EPO application No. 83304614.7, published on Apr. 4, 1984, discloses antifungal 1-aryl-1-perfluoroalkyl-2-(1H-1,2,4-triazol-1-yl)ethanols of the formula

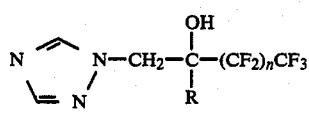

wherein R is 5-chloropyrid-2-yl- or phenyl optionally substituted with from one to three substituents selected from halo, $CF_3$, $(C_{1-4})$alkyl or $(C_{1-4})$alkoxy; and n is 0 or an integer from 1 to 5.

SUMMARY OF THE INVENTION

According to the invention, there are provided compounds of the formula:

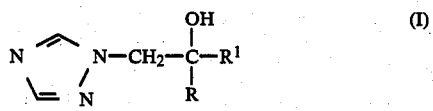

where R is a phenyl group optionally substituted by 1 to 3 substituents each independently selected from F, Cl, Br, I, trifluoromethyl, $C_1$-$C_4$ alkyl and $C_1$-$C_4$ alkoxy, or R is a 5-chloropyrid-2-yl group;

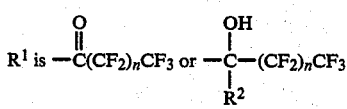

where n is 0, 1, 2 or 3 and $R^2$ is H or $C_1$-$C_4$ alkyl; and their pharmaceutically and agriculturally acceptable salts.

The invention also provides a pharmaceutical composition comprising a compound of the formula (I) or a pharmaceutically acceptable salt thereof, together with a pharmaceutically acceptable diluent or carrier.

The invention further provides a compound of the formula (I) or a pharmaceutically acceptable salt thereof, for use in medicine, in particular for treating a fungal infection in an animal, including a human being.

The invention further includes a fungicidal composition for agricultural use, comprising a compound of the formula (I), or an agriculturally acceptable salt thereof, together with an agriculturally acceptable diluent or carrier.

It also provides a method of treating an animal, including a human being, having a fungal infection, which comprises administering to said animal an effective amount of a compound of the formula (I) or pharmaceutically acceptable salt thereof.

The invention also includes a method of treating a seed or plant having a fungal infection, which comprises contacting said seed or plant or the locus thereof, with an antifungally effective amount of a compound of the formula (I) or agriculturally acceptable salt thereof.

When R is said optionally substituted phenyl group, it is preferably phenyl substituted by 1 to 3 substituents, more preferably 1 or 2 substituents, each independently selected from F, Cl, Br, I and $CF_3$. In particular in this aspect, R is 4-fluorophenyl, 4-chlorophenyl, 4-trifluoromethylphenyl, 2-fluorophenyl, 2,4-dichlorophenyl, 2,4-difluorophenyl, 2-fluoro-4-chlorophenyl, 2,5-difluorophenyl, 2,4,6-trifluorophenyl or 4-bromo-2,5-difluorophenyl.

R is most preferably 2,4-difluorophenyl, 2,4-dichlorophenyl, 4-chlorophenyl or 4-fluorophenyl.

"n" is preferably 1 or 2. $R^2$ is preferably H, $CH_3$ or $C_2H_5$.

In the preferred individual compound, R is 2,4-difluorophenyl and $R^1$ is $-C(OH)(CH_3)C_2F_5$.

The hydroxy-ketones of the formula (I) can be prepared by the following general route:

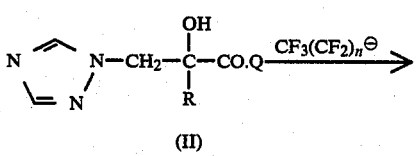

(IA)

where R and n are as defined for formula (I) and Q is a leaving group, preferably $C_1$-$C_4$ alkoxy.

The anion $CF_3(CF_2)_n^\ominus$ is preferably supplied by using the Grignard reagent $CF_3(CF_2)_n$MgI or $CF_3(CF_2)_n$MgBr, typically as a mixture thereof preparable from $CF_3(CF_2)_n$I and methylmagnesium bromide. Thus in a typical reaction, the iodide $CF_3(CF_2)_n$I in a suitable solvent, e.g. dry ether, is reacted with methylmagnesium bromide at $-65°$ to $-70°$ C. After stirring at this temperature for about ½ hour, the compound (II) in e.g. dry ether is slowly added, keeping the temperature at $-65°$ C. or below. After stirring at this temperature for about 1 hour, the mixture is allowed to slowly warm to about $-25°$ C. Aqueous ammonium chloride solution is then added, and the separated ether layer is washed with water. The aqueous layer is extracted with ether. The combined ethereal extracts are then dried ($MgSO_4$), evaporated, and the residue is chromatographed on silica in conventional manner to give the title compound.

The starting materials of the formula (II) can be prepared conventionally, e.g.:

-continued

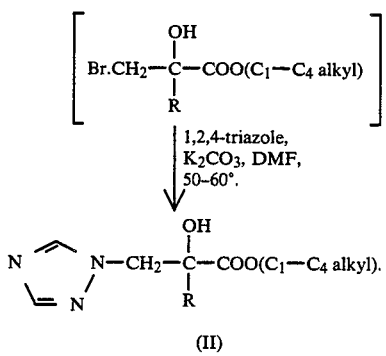

(II)

It is most preferred to use the ethyl ester.

The diols of the formula (I) in which $R^2$ is H can be prepared by the reduction of the ketones of the formula (IA) in a conventional manner. It is preferred to use sodium borohydride as the reducing agent.

The diols of the formula (I) in which $R^2$ is $C_1$–$C_4$ alkyl can be prepared by the reaction of the ketones (IA) with a reagent of the formula ($C_1$–$C_4$ alkyl).X where X is MgBr, MgI or Li in a conventional manner.

The compounds of the invention contain either one or two optical centers. In compounds which contain one optical center the invention includes both resolved and unresolved forms. In compounds which contain two optical centers the invention includes both resolved and unresolved forms of each diastereomer.

Pharmaceutically acceptable acid addition salts of the compounds of the formula (I) are those formed from strong acids which form non-toxic acid addition salts, such as hydrochloric, hydrobromic, sulphuric, oxalic and methanesulphonic acids.

The salts may be obtained by conventional procedures, e.g. by mixing solutions containing equimolar amounts of the free base and desired acid, and the required salt is collected by filtration, if insoluble, or by evaporation of the solvent.

Also included are the alkali metal salts, preparable conventionally.

The compounds of the formula (I) and their pharmaceutically acceptable salts are antifungal agents, useful in combating fungal infections in animals, including humans. For example they are useful in treating topical fungal infections in man caused by, among other organisms, species of Candida, Trichophyton, Microsporum or Epidermophyton, or in mucosal infections caused by *Candida albicans* (e.g. thrush and vaginal candidiasis). They can also be used in the treatment of systemic fungal infections caused by, for example, *Candida albicans, Cryptococcus neoformans, Aspergillus fumigates,* Coccidioides, Paracoccidioides, Histoplasma or Blastomyces.

The in vitro evaluation of the antifungal activity of the compounds can be performed by determining the minimum inhibitory concentration (m.i.c.) which is the concentration of the test compounds in a suitable medium at which growth of the particular micro-organism fails to occur. In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other micro-organisms used in such tests can include *Cryptococcus neoformans, Aspergillus fumigatus,* Trichophyton spp; Microsporum spp; *Epidermophyton floccosum, Coccidioides immitis* and *Torulopsis glabrata.*

The in vivo evaluation of the compounds can be carried out at a series of dose levels by intraperitoneal or intravenous injection or by oral administration to mice which are inoculated with a strain of *Candida albicans.* Activity is based on the survival of a treated group of mice after the death of an untreated group of mice following 48 hours observation. The dose level at which the compound provides 50% protection against the lethal effect of the infection is noted.

For human use, the antifungal compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) will be from 0.1 to 5 mg/kg (in divided doses) when administered by either the oral or parenteral route. Thus tablets or capsules of the compounds will contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) and their salts also have activity against a variety of plant pathogenic fungi, including for example various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Micro-organisms used in such tests include *Cochliobolus carbonum, Pyricularia oryzae, Glomerella cin-*

*gulata, Penicillium digitatum, Botrytis cinerea* and *Rhizoctonia solani.*

For agricultural and horticultural purposes the compounds and their agriculturally acceptable salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be applied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack.

The following Examples illustrate the invention. All temperatures are in °C.:

EXAMPLE 1

(A.) Preparation of 1-(ethoxycarbonyl)-1-(4-fluorophenyl)-2-(1H-1,2,4-triazol-1-yl)ethanol

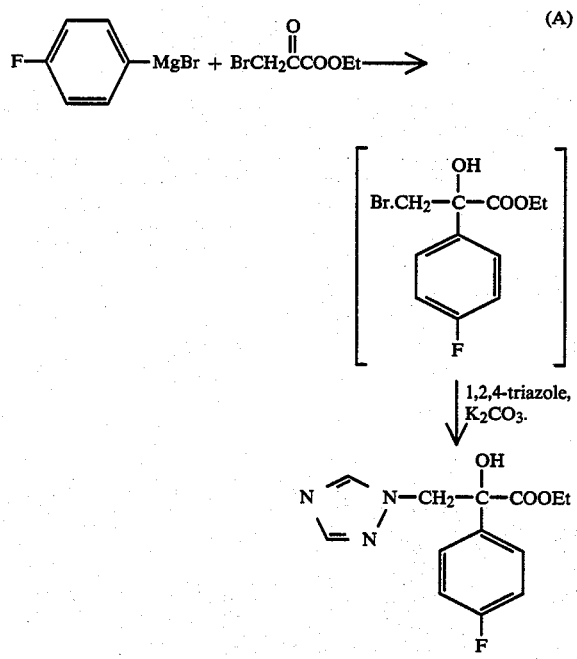

p-Fluorobromobenzene (50 g., 0.29M) was treated with magnesium turnings (10 g., 0.42M) in dry ether (200 ml) to form the Grignard derivative. The resulting solution of the Grignard reagent was added to a solution of ethyl bromopyruvate (46.4 g., 0.24M) in dry ether (300 ml.) and the solution was kept at between −70° and −65° for about 2 hours. The mixture was then stirred at −70° for ½ hour and was then allowed to warm to −30° over ½ hour. Keeping the temperature below 0°, ammonium chloride (100 g.) in water (300 ml.) was added and the solution was then allowed to warm to room temperature (20°). The ether layer was separated and the aqueous layer was extracted with ether (2×500 ml.). The combined ether fractions were dried (MgSO$_4$) and evaporated. The resulting crude intermediate (A) was reacted with 1,2,4-triazole (50 g., 0.72M) and anhydrous potassium carbonate (100 g., 0.72M) in dry dimethylformamide (300 ml.) at 50°–60° for about 4 hours. The mixture was then allowed to cool to room temperature (20°) and ether (500 ml.) was added. The ether layer was washed with water (500 ml.) and the aqueous layer was extracted with ether (2×500 ml.). The combined ethereal fractions were washed with water (3×200 ml.), dried (MgSO$_4$) and evaporated to give the crude title compound. Chromatography on silica (230–400 mesh) and eluting with ethyl acetate followed by trituration with petrol (60°–80°) gave the title compound (20 g., 30% yield). A small sample was characterised as the methanesulphonate salt, m.p. 142°–144°, which was prepared by reaction with methanesulphonic acid in dry ether followed by recrystallisation from ethyl acetate.

Analysis %: Found: C: 45.1; H: 4.9; N: 11.1; Calculated for $C_{13}H_{14}FN_3O_3.CH_3SO_3H$: C: 44.8; H: 4.8; N: 11.2.

(B.) Preparation of 2-hydroxy-2-(4-fluorophenyl)-4,4,5,5,5-pentafluoro-1-(1H-1,2,4-triazol-1-yl)pentan-3-one

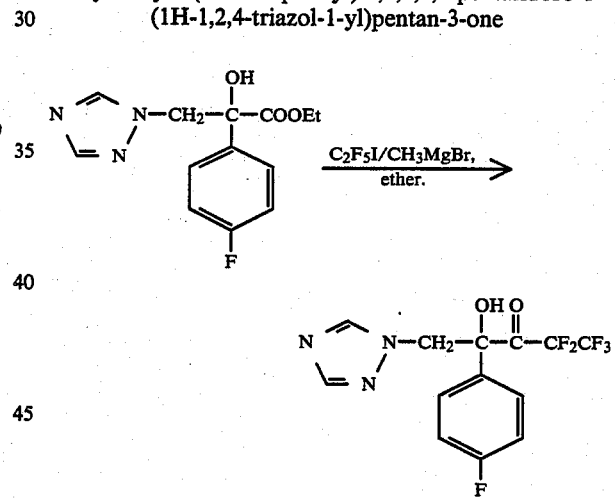

Gaseous pentafluoroethyl iodide (5 g., 0.02M) was passed into a flask containing dry ether (40 ml.) at −70° and fitted with a dry-ice condenser. A 3 molar solution of methylmagnesium bromide (5.8 ml., 0.017M) was then added over 5 minutes keeping the temperature between −70° and −65°. The mixture was then stirred at −70° for ½ hour. 1-Ethoxycarbonyl-1-(4-fluorophenyl)-2-(1H-1,2,4-triazol-1-yl)ethanol (1.3 g., 0.0047M) in dry ether (10 ml.) was then added over 10 minutes keeping the temperature at −65° or below. The mixture was then stirred at −70° for 1 hour and was then allowed to warm to −25° over 1½ hours. A solution of ammonium chloride (5 g.) in water (30 ml.) was then added. The ether layer was separated and the aqueous layer was extracted further with ether (2×40 ml.). The ether layers were combined, dried (MgSO$_4$) and evaporated to give the crude title compound as an oil. The oil was purified by chromatography on silica (230–400 mesh) eluting with ethyl acetate:60°–80° petrol (4:1, by volume) to give the title compound, 1.2 g (55% yield). The compound was recrystallised from cyclohexane, m.p. (after said recrystallisation) 128°–132°.

Analysis %: Found: C: 44.3; H: 2.6; N: 11.7; Calculated for $C_{13}H_9F_6N_3O_2$: C: 44.2; H: 2,6; N: 11.9.

EXAMPLES 2 TO 5

The following compounds were prepared similarly to Example 1 parts (A) and (B) from appropriate starting materials:

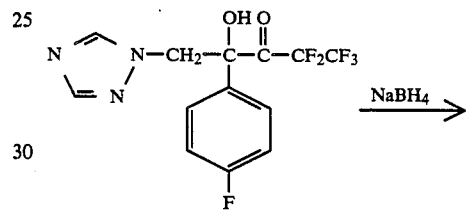

| Example No. | R | $R^1$ | m.p. (°C.) | Analysis % (Theoretical in brackets) | | |
|---|---|---|---|---|---|---|
| | | | | C | H | N |
| 2 | 4-F-C6H4 | —C(CF2)2CF3 (=O) | 130–133 | 41.6 (41.7 | 2.2 2.25 | 10.4 10.4) |
| 3 | 2,4-F2-C6H3 | —CCF2CF3 (=O) | 147–150 | 42.0 (42.1 | 2.2 2.2 | 11.1 11.3) |
| 4 | 2,4-Cl2-C6H3 | —CCF2CF3 (=O) | 151–3 | 38.9 (38.6 | 2.1 2.0 | 10.5 10.4) |
| 5 | 4-Cl-C6H4 | —CCF2CF3 (=O) | 100–1 | 42.0 (42.2 | 2.4 2.45 | 11.4 11.4) |

The ester starting materials prepared in the first stage (Part A) were characterised as follows:

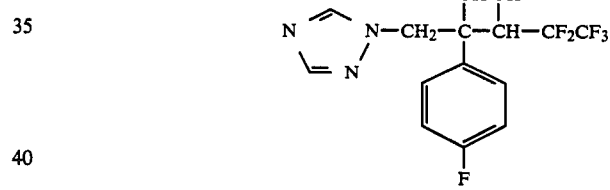

| R | m.p. (°C.) | Analysis % (Theoretical in brackets) | | |
|---|---|---|---|---|
| | | C | H | N |
| 2,4-F2-C6H3 (characterised as methanesulphonate salt) | 117–9 | 42.45 (42.75 | 4.3 4.4 | 10.6 10.7) |
| 2,4-Cl2-C6H3* | 126–128 | 47.1 (47.3 | 4.0 4.0 | 12.8 12.7) |

| R | m.p. (°C.) | Analysis % (Theoretical in brackets) | | |
|---|---|---|---|---|
| | | C | H | N |
| 4-Cl-C6H4 | 50–52 | 53.8 (52.8 | 5.2 4.8 | 14.0 14.2) |

*Prepared using 2,4-dichloroiodobenzene.

EXAMPLE 6

Preparation of 2-(4-fluorophenyl)-4,4,5,5,5-pentafluoro-1-(1H-1,2,4-triazol-1-yl)pentan-2,3-diol

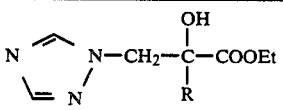

2-Hydroxy-2-(4-fluorophenyl)-4,4,5,5,5-pentafluoro-1-(1H-1,2,4-triazol-1-yl)pentan-3-one (0.2 g., 0.00057M) was dissolved in isopropyl alcohol (10 ml.) and the resulting solution was cooled in ice. Sodium borohydride (0.2 g., 0.005M) was then added, and the mixture was stirred for 1 hour whilst being cooled in an ice bath. Hydrochloric acid (2N, 10 ml.) was then added. The isopropyl alcohol was evaporated, the remaining solution was treated with dilute aqueous sodium bicarbonate solution to neutrality, and the mixture was extracted with methylene chloride (3×10 ml). The combined methylene chloride extracts were dried (MgSO4) and evaporated. Chromatography of the residue on silica (230–400 mesh) using ethyl acetate as the eluant gave the pure title compound, 0.09 g., which was then recrystallised from ethyl acetate/60°–80° petrol, m.p. (after said recrystallisation) 165°–168°.

Analysis %: Found: C: 44.2; H: 3.1; N: 11.9; Calculated for $C_{13}H_{11}F_6N_3O_2$: C: 43.95; H: 3.1; N: 11.8.

EXAMPLES 7 TO 9

The following compounds were prepared similarly to Example 6 by the sodium borohydride reduction of the corresponding ketone:

$$\underset{N}{\overset{N}{\Vert}}\hspace{-0.3em}\underset{N}{\diagdown}N-CH_2-\underset{R}{\overset{OH}{\underset{|}{C}}}-R^1$$

| Example No. | R | R¹ | m.p. (°C.) | Analysis % (Theoretical in brackets) | | |
|---|---|---|---|---|---|---|
| | | | | C | H | N |
| 7 | 2,4-difluorophenyl-methyl | —CH(OH)CF₂CF₃ | 197–199 | 41.9 (41.8 | 2.5 2.7 | 11.2 11.3) |
| 8 | 4-fluorophenyl-methyl | —CH(OH)(CF₂)₂CF₃ | 145–148 | 41.4 (41.5 | 2.7 2.7 | 10.3 10.4) |
| 9 | 2,4-dichlorophenyl-methyl | —CH(OH)CF₂CF₃ | 200–203 | 38.4 (38.4 | 2.5 2.5 | 10.2 10.35) |

EXAMPLE 10

Preparation of 2-(2,4-difluorophenyl)-3-methyl-4,4,5,5,5-pentafluoro-1-(1H-1,2,4-triazol-1-yl)pentane-2,3-diol

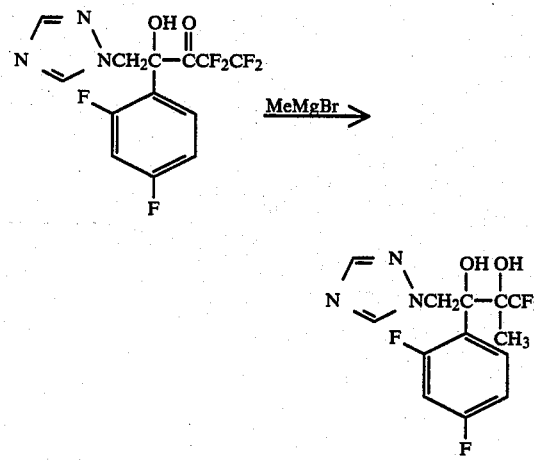

2-(2,4-Difluorophenyl)-2-hydroxy-4,4,5,5,5-pentafluoro-1-(1H-1,2,4-triazol-1-yl)pentan-3-one (0.5 g; 0.00135 moles) was dissolved in sodium-dried diethyl ether (50 cm³) and methylmagnesium bromide (1.35 cm³ of a 3M solution in ether; 0.00405 moles) was added. Dry tetrahydrofuran (15 cm³) was then added. The mixture was heated at reflux for 2 hours, cooled and 5% aqueous ammonium chloride (50 cm³) was added, followed by ethyl acetate (100 cm³). The phases were separated and the organic phase was dried (MgSO₄) and evaporated. The residue was purified by flash column chromatography on 230–400 mesh silica, eluting with ethyl acetate:diethylamine (95:5, 500 cm³). Two diastereomers were recovered by collection and evaporation of appropriate fractions. The first diastereomer to be eluted was called diastereomer I.

Diastereomer I
  Yield: 123 mg
  Melting Point: 148°–150°.
  Analysis %: Found: C: 43.7; H: 3.15; N: 10.7 Calculated for C₁₄H₁₂F₇N₃O₂: C: 43.4; H: 3.1; N: 10.8.
Diastereomer II
  Yield: 60 mg
  Melting Point: 127°–129°.
  Analysis %: Found: C: 43.5; H: 3.1; N: 10.8 Calculated for C₁₄H₁₂F₇N₃O₂: C: 43.4; H: 3.1; N: 10.8.
  The total yield was 183 mg (35%).

EXAMPLES 11–13

The following compounds were prepared similarly to Example 10 from the appropriate ketone and either MeMgBr or EtMgBr:

$$\underset{N}{\overset{N}{\Vert}}\hspace{-0.3em}\underset{N}{\diagdown}N-CH_2-\underset{R}{\overset{OH}{\underset{|}{C}}}-\underset{R^2}{\overset{OH}{\underset{|}{C}}}-C_2F_5$$

| Example No. | R | R² | m.p. (°C.) | Analysis % (Theoretical in brackets) | | |
|---|---|---|---|---|---|---|
| | | | | C | H | N |
| 11 | 4-fluorophenyl-methyl | CH₃ | Diastereomer I: 207–9 | 45.5 (45.4 | 3.65 3.55 | 11.4 11.4) |
| | | | Diastereomer II: 173–4 | 45.7 (45.5 | 3.55 3.55 | 11.4 11.4) |
| 12 | 4-chlorophenyl-methyl | CH₃ | Diastereomer I: 184–5 | 43.6 (43.8 | 3.4 3.5 | 10.9 11.0) |
| | | | Diastereomer II: 174–6 | 43.5 (43.8 | 3.4 3.5 | 10.9 11.0) |
| 13 | 2,4-difluorophenyl-methyl | C₂H₅ | Diastereomer I: 110–112 | 45.35 (44.9 | 3.6 3.5 | 10.2 10.5) |
| | | | Diastereomer II: 174–6 (as monohydrate) | 43.1 (42.9 | 3.3 3.3 | 9.9 10.0) |

Using the test method described in the text, the PD₅₀ values (p.o.; 48 hours) for the compounds of the Examples against *Candida albicans* in mice are as follows:

| Product of Example No. | PD₅₀ (p.o., mg./kg.) |
|---|---|
| 1(B) | 0.7 |
| 2 | 1.4 |
| 3 | <1.0 |
| 4 | <1.0 |
| 5 | <1.0 |
| 6 | <1.0 |
| 7 | <1.0 |
| 8 | 3.1 |
| 9 | <1.0 |
| 10 diastereomer I | <1.0 |
| diastereomer II | <1.0 |
| 11 diastereomer I | <1.0 |
| diastereomer II | <1.0 |
| 12 diastereomer I | <1.0 |
| diastereomer II | <1.0 |
| 13 diastereomer I | 1.3 |
| diastereomer II | <1.0 |

We claim:
1. A compound of the formula:

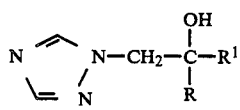 (I)

or a pharmaceutically or agriculturally acceptable salt thereof, wherein R is 5-chloropyrid-2-yl or a phenyl group optionally substituted by 1 to 2 substituents each independently selected from F or Cl; and

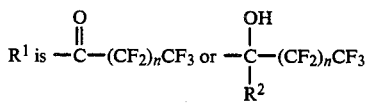

where n is 1 or 2, and $R^2$ is H or $C_1$–$C_4$ alkyl.

2. A compound as claimed in claim 1, wherein R is phenyl substituted by 1 to 2 substituents each independently selected from F or Cl.

3. A compound as claimed in claim 2 wherein R is 4-chlorophenyl, 4-fluorophenyl, 2,4-dichlorophenyl or 2,4-difluorophenyl.

4. A compound as claimed in claim 3 wherein $R^2$ is H, $CH_3$ or $C_2H_5$.

5. A compound as claimed in claim 4 wherein $R^2$ is H or $CH_3$.

6. The compound as claimed in claim 5 wherein R is 2,4-difluorophenyl and $R^1$ is —C(OH)(CH$_3$)C$_2$F$_5$.

7. The compound as claimed in claim 5 wherein R is 4-fluorophenyl and $R^1$ is —C(OH)(CH$_3$)C$_2$F$_5$.

8. A compound as claimed in claim 2 wherein $R^1$ is

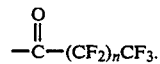

9. The compound as claimed in claim 8 wherein R is 2,4-difluorophenyl and $R^1$ is

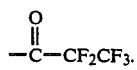

10. The compound as claimed in claim 8 wherein R is 4-fluorophenyl and $R^1$ is

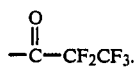

11. A fungicidal composition comprising a compound according to claim 1 or a pharmaceutically or agriculturally acceptable salt thereof, together with a pharmaceutically or agriculturally acceptable diluent or carrier.

12. A method of treating a plant or seed having a fungal infection, which comprises contacting said plant or seed or the locus thereof with an antifungally effective amount of a compound according to claim 1.

13. A method of treating a fungal infection in a human which comprises administering to said human an antifungally effective amount of a compound according to claim 1.

* * * * *